United States Patent [19]

Higuchi et al.

[11] 3,953,392

[45] *Apr. 27, 1976

[54] STYRENE RESIN COMPOSITION

[75] Inventors: Masaru Higuchi; Hajime Ohnishi; Hiroshi Yagihara, all of Saitama, Japan

[73] Assignee: Daicel Ltd., Osaka, Japan

[ * ] Notice: The portion of the term of this patent subsequent to May 13, 1992, has been disclaimed.

[22] Filed: Jan. 27, 1975

[21] Appl. No.: 544,055

Related U.S. Application Data

[60] Division of Ser. No. 376,318, July 5, 1973, Pat. No. 3,883,464, and a continuation-in-part of Ser. No. 212,787, Dec. 27, 1971, Pat. No. 3,817,900.

[30] Foreign Application Priority Data

Dec. 30, 1970 Japan............................... 45-122245
Nov. 17, 1971 Japan............................... 46-92284

[52] U.S. Cl..................... 260/30.4 A; 260/30.4 N; 260/45.8 A; 260/348.5 L; 260/880 R
[51] Int. Cl.²........................ C08K 5/13; C08K 5/15
[58] Field of Search................ 260/30.4 R, 30.4 N, 260/30.4 A, 45.8 A, 880 R, 348.5 L

[56] References Cited
UNITED STATES PATENTS

| | | | |
|---|---|---|---|
| 3,629,370 | 12/1971 | Ott et al. | 260/880 R |
| 3,658,743 | 4/1972 | Berilaequa | 260/45.8 A |
| 3,883,464 | 5/1975 | Higuchi et al. | 260/30.4 R |

*Primary Examiner*—Donald E. Czaja
*Assistant Examiner*—H. H. Fletcher
*Attorney, Agent, or Firm*—Woodhams, Blanchard and Flynn

[57] ABSTRACT

Novel styrene resin compositions, especially styrene-acrylonitrile resin and styrene-acrylonitrile-butadiene resin compositions, are provided, which comprise a styrene resin having blended therein as lubricant at least one of the compounds represented by the following general formula:

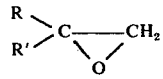

wherein R and R' each represent hydrogen or a straight chain, saturated alkyl radical, the sum of the carbon atoms in both radicals R and R', being 14–42.

8 Claims, 1 Drawing Figure

U.S. Patent   April 27, 1976   3,953,392
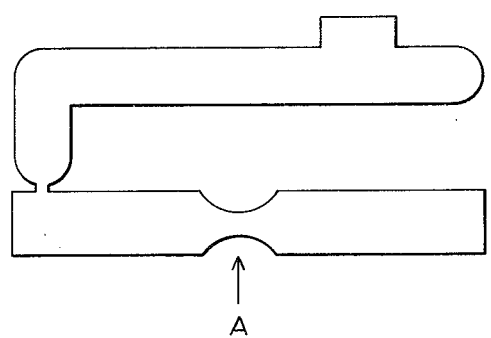

STYRENE RESIN COMPOSITION

This application is a division of application Serial No. 376,318, filed July 5, 1973, now U.S. Pat. No. 3,883,464, which in turn is a continuation-in-part of application Ser. No. 212,787, filed Dec. 27, 1971, now U.S. Pat. No. 3,817,900.

The present invention relates to a styrene resin composition containing as lubricant for molding and fabricating of said resin at least one of the compounds represented by the general formula:

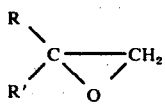

wherein R and R' each represent hydrogen or a straight chain, saturated alkyl radical, and the sum of the carbon atoms in both radicals R and R' is 14–42.

In general, lubricants for plastics increase the fluidity of the plastics and prevent the plastics from sticking or adhering to parts of molding machines. The lubricants, therefore, are important for improving the workability and processibility of the plastics. As such lubricants for styrene resin plastics as mentioned above, there have been used various materials such as silicon resins, paraffin waxes, higher fatty acids and the salts thereof, higher alcohols and higher fatty amides. The properties required for lubricants are, in addition to flow promotion properties, that they do not cause decomposition or coloring in the course of the process and they do not cause plate-out or do not harm transparency. However, a lubricant which satisfies all of these requirements has not been known.

We have found that the compounds of the general formula shown above:

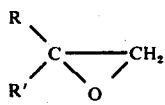

wherein R and R' have the same meanings as above exhibit not only excellent flow promotion properties but also other effects desirable for lubricants when incorporated in styrene resin plastics such as described above to be molded. Namely, they are stable at a high temperature and they do not cause decomposition, coloring or plate-out, thereby yielding quite transparent products. The present invention has been accomplished on the basis of these findings.

As the compounds of the above general formula

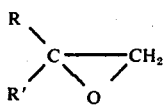

wherein one of R and R' represents hydrogen, there may be mentioned, for example, 1,2-epoxyhexadecane, 1,2-epoxyheptadecane, 1,2-epoxyoctadecane, 1,2-epoxynonadecane, 1,2-epoxyeicosane, 1,2-epoxyheneicosane, 1,2-epoxydocosane, 1,2-epoxytricosane, 1,2-epoxytetracosane, 1,2-epoxypentacosane, 1,2-epoxyhexacosane, 1,2-epoxyheptacosane, 1,2-epoxyoctacosane, 1,2-epoxynonacosane, 1,2-epoxytriacontane, 1,2-epoxyhentriacontane, 1,2-epoxydotriacontane, 1,2-epoxytritriacontane, 1,2-epoxytetratriacontane, 1,2-epoxypentatriacontane, 1,2-epoxyhexatriacontane, 1,2-epoxyheptatriacontane, 1,2-epoxyoctatriacontane, 1,2-epoxynonatriacontane, 1,2-epoxytetracontane, 1,2-epoxyhentetracontane, 1,2-epoxydotetracontane, 1,2-epoxytritetracontane and 1,2-epoxytetratetracontane. As the compounds of the above general formula wherein both R and R' represent an alkyl radical, there may be mentioned compounds (which may be used alone or in the form of a mixture of two or more compounds) containing a total of 14–42 carbon atoms in the two alkyl radicals R and R' such as ethyl, butyl, hexyl, octyl, decyl, dodecyl, tetradecyl, hexadecyl, octadecyl, eicosyl, docosyl, tetracosyl, hexacosyl, octacosyl, triacontyl, dotriacontyl, tetratriacontyl, hexatriacontyl, octatriacontyl, tetracontyl and dotetracontyl. The compounds of the above general formula containing 43 or more carbon atoms have sufficient possibility of being used as lubricants, though they have not been tested due to the difficulty of synthesis of them on an industrial scale. The compounds of the present invention can be synthesized by, for example, treating an α-olefin of 16–44 carbon atoms, which is obtained, for example, by cracking of a higher paraffin wax or oligomerization of ethylene in a conventional method, with hydrogen peroxide or an organic peracid. The compounds can be synthesized also through chlorohydrin. These methods for the synthesis of the compounds of the present invention are referred to in D. Swern, et al., J. Am. Chem. Soc. 68, 1501 (1946); Chem. Rev. 45, 1 (1949); Org. Reaction, 7, 378 (1953); H. C. Wohlers, et al. Ind. Eng. Chem., 50, 1685 (1958); Masuo and Kato, Org. Synth. Chem. (Japan), 26, 367 (1968); Takagi, et al., Bulletin Ind. Chem. (Japan), 69, 1080, (1966), 70, 1446 (1967) and Oil Chem. (Japan), 16, 462, (1967).

Though the detailed mechanism of the action of the lubricants on styrene resin plastics is still unknown, at least a moderate compatibility with the plastics to be treated is required. If the compatibility is too high, the lubricants act as internal plasticizers and, on the other hand, if compatibility is too low, they cause plate-out. Thus, too high and too low compatibilities are not desirable for the lubricants.

The compounds used in the present invention contain in a molecule a long chain alkyl radical as nonpolar component and an epoxy radical as polar component. The lubricants possess a suitable compatibility with styrene resin plastics which results from a good balance between said nonpolar and polar components and, consequently, they act as excellent lubricants in the process for molding and fabricating styrene resin plastics. As the styrene resin plastics to be used in the styrene resin composition of the present invention, there may be mentioned copolymers of at least one monomer selected from the group of monomers listed in the following (1) with at least one monomer selected from the group of monomers listed in the following (2).

1. styrene, α-methyl styrene and various nuclear substituted styrenes
2. acrylonitrile, acrylic esters and methacrylic esters, such as methyl, ethyl and butyl esters.

Such copolymers include graft copolymers containing rubber components.

Among the above styrene resins, preferred styrene resins to be used in the present invention are acrylonitrile-styrene (AS) copolymer resins consisting of 10 to 50 percent by weight of acrylonitrile and 50 to 90 percent by weight of styrene and also acrylonitrile-butadiene-styrene (ABS) copolymer resins containing 3 to 50 percent by weight of a rubber component and the balance of a monomer mixture of styrene and acrylonitrile, which monomers are graft copolymerized on the rubber in the above weight ratio of 50–90: 10–50.

The preparation methods of ABS resins are classified generally into (a) blend method, (b) graft method and (c) graft-blend method. Among these methods, the blend method was first known, wherein ABS resins were produced by a mechanical mixing of AS resins with a nitrile rubber. On the other hand, according to the socalled graft method, ABS resins are produced by the graft polymerization of styrene and acrylonitrile under the existence of a rubber component, in which the copolymerization reaction of styrene and acrylonitrile, the grafting reaction onto the rubber component and the cross-linking reaction proceed simultaneously. The chemical reactions caused in such graft method are complicated and have not yet been fully clarified, but, according to the prior art literatures, the AS resins grafted on the rubbery material are usually in the range of 50 to 200% by weight based on the weight of the rubber component. As the ABS resins to be used in the present invention, those produced by the socalled graft method or graft-blend method are preferred, because these ABS graft copolymer resins are far superior to the ABS resins produced by the blend method in their mechanical strength. (Refer to R. N. Haward and J. Mann : Pro. Royal Soc. 282A (1964) p.133; E. M. Bevilacqua and O. W. Lunstedt : J. Poly. Sci., 24 (1957) p.297; A. D. McIntyre : J. Appl. Poly Sci., 5 (1961) p.195; B. D. Gesner : J. Polymer Sci. A-3 page 3825 (1965))

The above lubricant compounds used in the present invention are effective both for AS resins and ABS resins irrespective of the existence or non-existence of rubber components. This is shown by the fact that, in either of AS and ABS resins, the increase of the injection pressure is possible in the injection molding of the resin compositions. Further, even in the case where tetrabromobisphenol A, a typical additive having a low compatibility with styrene resins, is used, the lubricant compounds of the present invention have a remarkable effect of increasing the compatibility of such resins with tetrabromobisphenol A, which results in the increase of the injection pressure and the prevention of coloring of resins within the molding machine. These effects are remarkable and have not been known in prior art rubber or plastic compositions containing epoxy compounds as an additive. The optimum amount of the lubricant to be used varies depending upon the kinds of styrene resin plastics to be treated. However, a sufficient effect can be usually obtained by 0.01 – 3% by weight of the lubricant based on the styrene resin plastics. With respect to lubricant compounds having total carbon atoms of 14 to 28 in R and R', it is preferable to use the same in an amount of 0.05 – 2%, while, with respect to lubricant compounds having total carbon atoms of 29 to 42 in R and R', it is preferable to use same in an amount of 0.01 – 2%.

The incorporation of the lubricant and other additives in styrene resin compositions may be effected by a usual manner known in the art. The lubricant compound should be preferably dispersed uniformly in the resin. The styrene resin composition incorporated with the lubricant and other additives can be molded by any conventional means such as injection molding, plastication, flow molding, calendering, extrusion, foaming and thermofusion. As mentioned above, the lubricant of the present invention can lower the friction between the polymers during the molding and simultaneously it can reduce the friction between the polymer and the wall surfaces of the molding machine, thus enabling the easy adjustment of the molding temperature, which results in lowering the degree of distortion of the final molded product. Further, in the above processing, the epoxy compound lubricant of the present invention will not react with the styrene resin but will act stably on the resin as a lubricant. Probably, the lubricant compound will be oriented on the metal surface of the molding machine so as to increase the lubricant concentration on the wall surface, thus effecting the outer lubricity. Accordingly, different from the case of the molding of thermosetting resins, in which the flow of the resin is not important during the molding operation or from the case of the curing of such polymers as rubbers, in which the curing of the polymer should be carried out, the lubricants of the present invention show a very remarkable and excellent effect on such styrene resins as described above. The above lubricant compounds used in the present invention are stable to heat, light and air at the time of and after the addition or during and after the processing. Poorer properties in mechanical characteristics of the styrene resins due to decomposition, coloring or deterioration are thus not observed. The lubricants according to the present invention may be used alone or in the form of a mixture of two or more compounds of the above general formula. Particularly, transparency is improved as the carbon number of the compounds is widely distributed. The lubricants may be used together with known additives such as plasticizers, stabilizers, antioxidants, other lubricants, UV absorbing agents, flame retardants, colorants and antistatic agents.

Excellent properties of the lubricants of the present invention will be shown below by way of Preparations and Examples which, however, by no means limit the invention. In the following Examples, parts are by weight, unless otherwise specified.

The preparations show examples of the synthesis of the lubricant compounds of the present invention.

PREPARATION 1

133 parts of α-olefins of 20–30 carbon atoms (average molecular weight 334) were charged in a stainless steel reactor provided with a reflux condenser, stirrer, thermometer and dropping funnel and heated to 60°C. Then, 185 parts of peracetic acid solution [comprising 46.5% of ethyl acetate, 19.5% of peracetic acid, 0.5% of water, 0.03% of an organic phosphate of the formula $Na_5$-(2-ethylhexyl)$_5$-$(P_3O_{10})_2$ and the remainder of acetic acid] were added over one hour. Thereafter, the reaction was continued at an elevated temperature of 65°C for 3 hours and then at 70°C for one hour. After completion of the reaction, low boiling fractions were distilled out under reduced pressure and acetic acid was distilled out in a thin film evaporator to obtain 140.3 parts of the products, which will be referred to as lubricant [B] of the present invention hereinafter. Lubricant [B] comprised principally of (1) 75% of compounds of the general formula:

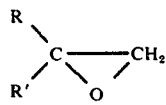

wherein either one of R and R' represents hydrogen and the other represents a straight chain, saturated alkyl radical of 18–28 carbon atoms and (2) 25% of compounds of the same formula wherein both R and R' represent a straight chain, saturated alkyl radical, total carbon atoms in both radicals being 18–28. IR analysis proved the existence of

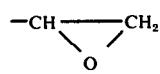

(3050, 1250, 915, 850 cm$^{-1}$). It was confirmed by chemical analysis that iodine value of the product was reduced from 76 to 2.0, and oxirane oxygen content was 4.1%.

PREPARATION 2

200 parts of mixed α-olefins of 30–44 carbon atoms (average molecular weight: 540) and 100 parts of benzene were charged in a stainless steel reactor provided with a reflux condenser, stirrer, thermometer and dropping funnel and heated to 64°C. After the solution in the reactor became homogeneous, 158 parts of peracetic acid solution [comprising 46.5% of ethyl acetate, 21.5% of peracetic acid, 0.5% of water, 0.03% of an organic phosphate of the structure Na$_2$-(2-ethylhexyl)$_5$(P$_3$O$_{10}$)$_2$ and the remainder of acetic acid] were added over one hour. Thereafter, the reaction was continued at an elevated temperature of 70°C for 4 hours. After completion of the reaction, the solvent was distilled out and acetic acid was then distilled out under reduced pressure to obtain 205.5 parts of the product, which will be referred to as lubricant [C] of the present invention hereinafter. lubricant [C] is principally comprises (1) 63% of compounds of the general formula:

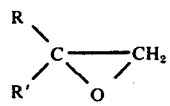

wherein either one of R and R' represents hydrogen atom and the other represents a straight chain, saturated alkyl radical of 28–42 carbon atoms and (2) 37% of compounds of the same general formula wherein both R and R' represent a straight chain saturated alkyl radical, the total carbon atoms in both radicals being 28–42. The existence of

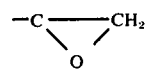

(3050, 1250, 915 and 850 cm$^{-1}$) was confirmed according to IR analysis. It was also confirmed that iodine value of the product was reduced from 47.1 and 2.0 and oxirane oxygen content was 2.5%.

In the drawing, FIG. 1 is a cross-sectional view of a test piece for tensile and impact strength tests.

EXAMPLE 1

100 parts of ABS resin (a graft copolymer obtained from 15 parts of styrene-butadiene rubber, 72 parts of styrene and 28 parts by weight of acrylonitrile) containing tetrabromobisphenol A were mixed with 0.1 part of the lubricant [A] (which is a 1 : 1 mixture of 1,2-epoxyhexadecane and 1,2-epoxyoctadecane), the lubricant [B] or the lubricant [C] of the present invention, respectively. The mixture was pelletized by a Bent-type extruder of 40 m/mφ. Then, the pellets were molded to a molded product (a test piece for the tensile and impact strength tests according to ASTM-D-1822) such as shown in FIG. 1 by an injection machine of inline screw type (TS-100 manufactured by Nissei Jushi). The evaluation of lubricity was indicated by the minumum injection pressure for molding under which the portion of the test piece indicated by A in FIG. 1 will cause whitening. In case the lubricity is excellent, no whitening will appear on the resin surface even by an injection at a high injection pressure and the mold releasing property of the molded product is good. Further, the discoloration and yellowing of the resin depending on its stay period in the cylinder were evaluated by using the above machine at cylinder temperatures of 210°C and 230°C and stay periods of 0, 5 and 10 minutes.

The test results are shown in Table 1. As is apparent from Table 1, the thermal stability of the self extingushing ABS resin, which resin is usually inferior in its lubricity and in its thermal stability at the time of molding, could be improved by the use of the lubricant according to the present invention. Further, the mechanical properties and the self extinguishing property of the molded products thus obtained were substantially equivalent to the corresponding molded products obtained with no addition of the lubricant.

Table 1

| Test No. | Composition Resin | Kinds of lubricant | Lubricity (minimum whitening pressure Kg/cm$^2$) | Evaluation of properties Discoloration during stay 210°C | | | Discoloration during stay 230°C | | |
|---|---|---|---|---|---|---|---|---|---|
| | | | | 0 min. | 5 min. | 10 min. | 0 min. | 5 min. | 10 min. |
| 1 | 100 parts | No addition | 70 | ● | ● | ○ | ○ | △ | X |
| 2 | " | [A] | 120 | ● | ● | ● | ● | ◕ | ● |
| 3 | " | [B] | 120 | ● | ● | ● | ● | ● | ● |

Table 1-continued

| Test No. | Composition Resin | Kinds of lubricant | Lubricity (minimum whitening pressure Kg/cm$^2$) | Evaluation of properties Discoloration during stay 210°C 0 min. | 5 min. | 10 min. | Discoloration during stay 230°C 0 min. | 5 min. | 10 min. |
|---|---|---|---|---|---|---|---|---|---|
| 4 | " | [C] | 110 | ● | ● | ● | ● | ● | ● |

Standard of evaluation:
● No change
○ Slight yellowing
△ Yellowing
X Burnt

EXAMPLE 2

100 parts of a heat-resistant ABS resin (a graft copolymer obtained from 10 parts of styrene-butadiene rubber, 40 parts of styrene, 27 parts of acrylonitrile and 33 parts of α-methyl styrene were added and uniformly mixed with 0.1 part of the lubricant [A], [B] or [C], respectively, and the lubricity of the obtained mixtures was evaluated according to the same method as described in Example 1. The results are shown in Table 2, from which it is seen that the lubricity of the ABS resin was remarkably improved by the addition of the lubricant according to the present invention.

Table 2

| Resin | Composition Kinds of lubricant | Evaluation of lubricity |
|---|---|---|
| 100 parts | No addition | Whitening at an injection pressure of more than 90 Kg/cm$^2$ |
| " | [A] | No whitening even at an injection pressure of 120 Kg/cm$^2$ |
| " | [B] | " |
| " | [C] | No whitening even at an injection pressure of 110 Kg/cm$^2$ |

EXAMPLE 3

100 parts of a general grade ABS resin (a graft copolymer obtained from 6 parts of styrene-butadiene rubber, 72 parts of styrene and 28 parts of acrylonitrile) were added and uniformly mixed with 0.1 part of the lubricant [A], [B] or [C], respectively, and the obtained mixtures were pelletized in the same manner as in Example 1. Then, their discoloration during their stay in the cylinder were respectively evaluated by using an injection machine of inline screw type (KY-100S manufactured by Kawagunchi Tekko). The results are shown in Table 3, from which it is seen that the lubricant compounds of the present invention can give a very excellent thermal stability to the ABS resin.

Table 3

| Resin | Composition Kinds of lubricant | Evaluation 260°C | 270°C | 290°C | 300°C |
|---|---|---|---|---|---|
| 100 parts | No addition | ○ | △ | X | X |
| " | [A] | ● | ● | ● | ● |
| " | [B] | ● | ● | ● | ○ |
| " | [C] | ● | ● | ● | ○ |

Standard of evaluation (comparison with the molded product made at a standard molding temperature of 225°C):
● No change
○ Slight yellowing
△ Yellowing
X Burnt

EXAMPLE 4

100 parts of a general grade styrene-acrylonitrile copolymer resin (27 parts of acrylonitrile, 73 parts of styrene, melt index : 4.8) or 100 parts of a high flow type styrene-acrylonitrile copolymer resin (27 parts of acrylonitrile, 73 parts of styrene, melt index : 10.3) were added with 0.1 part of the lubricant [A], respectively and the lubricities of the obtained mixtures were evaluated in the same manner as in Example 1. The results are shown in Table 4, from which it is seen that the lubricity of the AS resins was remarkably improved by the addition of the lubricant of the present invention.

Table 4

| Composition Kinds of resin | lubricant | Evaluation of lubricity Minimum whitening pressure Kg/cm$^2$ |
|---|---|---|
| General grade | No addition | 90 |
| " | [A] | 110 |
| High flow type | No addition | 80 |
| " | [A] | 110 |

The embodiments of the invention in which an exclusive property or privilege is claimed are defined as follows:

1. A thermoplastic synthetic resin moldable composition, consisting essentially of
   A. a synthetic resin consisting of (1) 3 to 50 percent by weight of rubber component,
   and the balance of said resin is (2) a copolymer grafted onto said rubber component, said copolymer consisting of
      a. from 50 to 90 percent by weight, based on said copolymer; of at least one first monomer component selected from the group consisting of styrene, α-methyl styrene and nucleus substituted styrenes, and the balance of said copolymer is
      b. at least one second monomer component selected from the group consisting of acrylonitrile and the methyl, ethyl and butyl esters of acrylic acid and methacrylic acid, said resin having blended therein,
   B. from 0.01 to 3.0 percent by weight, based on the weight of said resin, of one or a mixture of lubricants of the formula

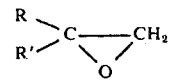

wherein R and R' each represent hydrogen or straight chain alkyl and the sum of the carbon atoms in R and R' is 14 to 42.

2. A composition according to claim 1, in which said copolymer (A2) consists of 50 to 90 percent by weight of styrene and the balance is acrylonitrile.

3. A composition according to claim 1, in which the sum of the carbon atoms in R and R' is 14 to 28, and the amount of said lubricant (B) is from 0.05 to 2 percent by weight, based on the weight of said resin (A).

4. A composition according to claim 1, in which the sum of the carbon atoms in R and R' is 29 to 42, and the amount of said lubricant (B) is from 0.01 to 2 percent by weight based on the weight of said resin (A).

5. A composition according to claim 2, containing tetrabromobisphenol A.

6. A composition according to claim 5, in which said lubricant consists of a mixture of compounds of said formula in which one of R and R' is hydrogen and the other is alkyl having 18 to 28 carbon atoms and compounds of said formula in which both of R and R' are alkyls and the total number of carbon atoms in R and R' is from 18 to 28.

7. A composition according to claim 5 in which said lubricant consists of a mixture of compounds of said formula in which one of R and R' is hydrogen and the other is alkyl having 28 to 42 carbon atoms and compounds of said formula in which both of R and R' are alkyls and the total number of carbon atoms in R and R' is from 28 to 42.

8. A composition according to claim 2, in which said rubber component is dispersed in a matrix of said copolymer.

* * * * *